(12) United States Patent
Mack

(10) Patent No.: US 11,827,599 B1
(45) Date of Patent: Nov. 28, 2023

(54) METHOD OF PREPARING IONIC FLUIDS

(71) Applicant: TETRA Technologies, Inc., The Woodlands, TX (US)

(72) Inventor: Arthur G. Mack, Conroe, TX (US)

(73) Assignee: TETRA Technologies, Inc., The Woodlands, TX (US)

(*) Notice: Subject to any disclaimer, the term of this patent is extended or adjusted under 35 U.S.C. 154(b) by 0 days.

(21) Appl. No.: 17/983,873

(22) Filed: Nov. 9, 2022

(51) Int. Cl.
C07D 207/04 (2006.01)

(52) U.S. Cl.
CPC .................. *C07D 207/04* (2013.01)

(58) Field of Classification Search
None
See application file for complete search history.

(56) References Cited

U.S. PATENT DOCUMENTS

| | | |
|---|---|---|
| 5,552,126 A | 9/1996 | Efraim et al. |
| 6,143,271 A | 11/2000 | Holdengraber et al. |
| 8,299,149 B2 | 10/2012 | Zilberman et al. |
| 9,453,285 B2 | 9/2016 | Ben-David et al. |
| 10,093,868 B1 | 10/2018 | Weers et al. |
| 2006/0094615 A1 | 5/2006 | Hecht et al. |
| 2019/0335763 A1 | 11/2019 | Zivkovic et al. |
| 2021/0101844 A1 | 4/2021 | Geinik et al. |

FOREIGN PATENT DOCUMENTS

| | | |
|---|---|---|
| EP | 2125621 B1 | 12/2014 |
| WO | WO2008109232 A1 | 9/2008 |
| WO | WO2013042109 A1 | 3/2013 |

OTHER PUBLICATIONS

Yao-Husuan Tseng, Yu-Yin Lee and Shih-Hsun Chen. "Synthesis of Quaternary Ammonium Room-Temperature Ionic Liquids and their Application in the Dissolution of Cellulose." Apr. 27, 2019, pp. 1-11, Appl. Sci. 2019, 9, 1750; doi:10.3390/app9091750.

Zheng Chang, Xukiong Wang, Yaqiong Yang, Jie Gao, Minxia Li, Lili Liu, and Yuping Wu. "Rechargeable Li//Br battery: a promising platform for post lithium ion batteries." 2014, pp. 19444-19450, J. Mater. Chem. A, 2014, 2, 19444.

D. Bryans, B.G. McMillan, M. Spicer, A. Wark, and L. Berlouis. "Complexing Additives to Reduce the Immiscible Phase Formed in the Hybrid ZnBr2 Flow Battery." Nov. 2, 2017, pp. A3342-A3348, Journal of the Electrochemical Society, 164 (13).

Grace Poon, Aishwarya Parasuraman, Tuti Mariana Lim, Maria Skyllas-Kazacos. "Electrochimica Acta. Evaluation of N-ethyl-N-methyl-morpholinium bromide as bromine complexing agents in vanadium bromide redox flow batteries." 2013, pp. 388-396, Electrochimica Acta 107.

Jack E. Baldwin and Martin Rudolph. "A Concise Approach to Kainoid Analogues." 1994, pp. 6163-6166, , Terahedron Letters, vol. 35, No. 33.

Laurence Mayrand-Provencher, Sixian Lin, Deborah Lazzerini, Dominic Rochefort. "Pyridinium-based protic ionic liquids as electrolytes for RuO2 electrochemical capacitors." 2010, pp. 5114-5121, Journal of Power Sources 195.

Uxua Jimenez-Blasco, Edurado Moreno, Maura Colera, Pilar Diaz-Carrasco, JoseC. Arrebola, Alvaro Caballero, Julian Morales, and Oscar A. Vargas. "Enhanced Performance of Zn/Br Flow Battery Using N-Methyl-N-Proplymorpholinium Bromide as Complexing Agent." 2021, pp. 1-15, Int. J. Mol. Sci. 2021, 22, 9288. https://doi.org/10.3390/ijms22179288.

*Primary Examiner* — Samantha L Shterengarts
(74) *Attorney, Agent, or Firm* — Roy Kiesel Ford Doody & North, APLC; Brett A. North

(57) ABSTRACT

A method of preparing MEP including the steps of: (a) adding N-methylpyrrolidine to an excess amount of ethyl bromide located in a reactor, wherein the N-methylpyrrolidine will react with the ethyl bromide forming MEP, wherein the reaction will have a reaction temperature that can varies over time; (b) stopping addition of N-methylpyrrolidine when the excess of ethyl bromide to the N-methylpyrrolidine falls within a range of 3:1 to 1.5:1; (c) adding water to the reactor creating a two phase system to develop which includes: (i) a top layer containing aqueous MEP and (ii) a bottom layer containing ethyl bromide; (d) separating the top layer from the bottom layer yielding a first aqueous solution of MEP and a second solution of ethyl bromide; and (e) removing N-methylpyrrolidine and ethyl bromide from the first aqueous solution of MEP.

22 Claims, 1 Drawing Sheet

METHOD OF PREPARING IONIC FLUIDS

BACKGROUND

Various embodiments relate to a low cost process to make quaternary ammonium compounds (ionic liquids or liquids to be used as electrolytes) for flow batteries for use in battery electrolytes as a bromine complexing agent. N-methyl-N-ethylpyrrolidinium ("MEP") is a quaternary ammonium complex.

While ordinary liquids such as water and gasoline are predominantly made of electrically neutral molecules, ionic liquids are largely made of ions. These substances are variously called liquid electrolytes, ionic melts, ionic fluids, fused salts, liquid salts, or ionic glasses.

Quaternary ammonium cations, also known as quats, are positively charged polyatomic ions of the structure $NR_4^+$ R being an alkyl group or an aryl group. Unlike the ammonium ion ($NH_4^+$) and the primary, secondary, or tertiary ammonium cations, the quaternary ammonium cations are permanently charged, independent of the pH of their solution. Quaternary ammonium salts or quaternary ammonium compounds (called quaternary amines in oilfield parlance) are salts of quaternary ammonium cations.

An ionic liquid is a salt in the liquid state. In some contexts, the term has been restricted to salts whose melting point is below some arbitrary temperature, such as 100° C. (212° F.). A salt, in chemistry, substance produced by the reaction of an acid with a base. A salt consists of the positive ion (cation) of a base and the negative ion (anion) of an acid. The reaction between an acid and a base is called a neutralization reaction. When in solution or the molten state, most salts are completely dissociated into negatively and positively charged ions and are good electrolytes (conductors of electricity).

Ionic liquids are usually prepared by a reaction of an alkyl halide (typically a bromide, such as ethyl bromide, which is a compound of bromine with another element or group, especially a salt containing the anion $Br^-$ or an organic compound with bromine bonded to an alkyl radical) with a tertiary amine (e.g.,N-methylpyrrolidine) in a solvent (e.g. acetonitrile) and then crystallizing the product and filtering to isolate the solid. The previously isolated solid is then dissolved in water to make an electrolyte solution that can be used in a flow battery. Water does not work well as a solvent in the reaction because it causes hydrolysis of ethyl bromide lowering the pH to less than 2 (see e.g., Example 4).

In organic chemistry, amines are compounds and functional groups that contain a basic nitrogen atom with a lone pair Amines are formally derivatives of ammonia, wherein one or more hydrogen atoms have been replaced by a substituent such as an alkyl or aryl group (these may respectively be called alkylamines and arylamines; amines in which both types of substituents are attached to one nitrogen atom may be called alkylarylamines). Various amines include amino acids, biogenic amines, trimethylamine, and aniline.

Alkyl halides are compounds in which one or more hydrogen atoms in an alkane have been replaced by halogen atoms (fluorine, chlorine, bromine or iodine). Alkyl halides can be classified as primary, secondary, or tertiary. Alkanes are organic compounds that consist entirely of single-bonded carbon and hydrogen atoms and lack any other functional groups. Alkanes have the general formula $C_nH_{2n+2}$ and can be subdivided into the following three groups: the linear straight-chain alkanes, branched alkanes, and cycloalkanes.

Bromine complexing agent are chemical species capable of binding with metal ions or other chemical entities in a system through its single or multiple sites. These sites have lone pairs of electrons which can be donated to the d orbitals of a metal ion, forming coordination bonds. This results in a coordination compound.

Most processes in the literature of preparing quaternary ammonium compounds utilize a solvent which is required to be removed after creation of the compounds.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the device illustrated and in its operation may be made without departing in any way from the spirit of the present invention. No feature of the invention is critical or essential unless it is expressly stated as being "critical" or "essential."

SUMMARY

In one embodiment a process is provided to make quaternary ammonium compounds (ionic liquids) in water.

In one embodiment is provided a method of making ionic liquids in water for flow batteries to be used in battery electrolytes as a bromine complexing agent.

In one embodiment is provided a method of making ionic liquids, without the need for solvents, in water for flow batteries to be used in battery electrolytes as a bromine complexing agent.

In one embodiment is provided a method of preparing MEP including the steps of: (a) adding N-methylpyrrolidine to an excess amount of ethyl bromide located in a reactor, wherein the N-methylpyrrolidine will react with the ethyl bromide forming MEP, wherein the reaction will have a reaction temperature that can varies over time; (b) stopping addition of N-methylpyrrolidine when the excess of ethyl bromide to the N-methylpyrrolidine falls within a range of 3:1 to 1.5:1; (c) adding water to the reactor creating a two phase system to develop which includes: (i) a top layer containing aqueous MEP and (ii) a bottom layer containing ethyl bromide; (d) separating the top layer from the bottom layer yielding a first aqueous solution of MEP and a second layer of ethyl bromide; and (e) removing trace amounts of unreacted N-methylpyrrolidine and ethyl bromide from the first aqueous solution of MEP.

In one embodiment the reactor can be a container, a tank, a vessel, a pressure vessel, a pipe, a conduit, or a flask. In one embodiment the reactor can be insulated such as by jacketing.

In one embodiment, during step "a" the reaction temperature is maintained lower than 50° C.

In one embodiment during step "b" the excess of ethyl bromide to the N-methylpyrrolidine remains reduces to be within a range of 3:1 to 1.85:1. In one embodiment the excess of ethyl bromide to the N-methylpyrrolidine reduces to be within a range of 2:1 to 1.85:1. In one embodiment the excess of ethyl bromide to the N-methylpyrrolidine reduces to be within a range of 3:1 to 2:1.

In one embodiment during step "b" a slurry of MEP is formed in the excess of ethyl bromide and this slurry of MEP and excess ethyl bromide is allowed to cool to 25° C. between steps "b" and "C".

In one embodiment during step "c" the water is purified water. Preferably, the purified water can be de-ionized water, reverse osmosis water, and/or distilled water.

In one embodiment step "d" is performed using a phase cut.

In one embodiment step "e" is performed by sparging with a noble gas to remove trace amounts of unreacted N-methylpyrrolidine and ethyl bromide from the first aqueous solution of MEP, which can be $N_2$. In one embodiment step "e" is performed by sparging with a gas is used for removal of trace amounts of unreacted N-methylpyrrolidine and ethyl bromide, wherein said gas is non-reactive relative to MEP, N-methylpyrrolidine, and ethyl bromide. In one embodiment the sparging is performed when the first aqueous solution of MEP is between 30° C. and 50° C. In one embodiment at the end of step "e" the pH is between 6 and 9. In one embodiment during step "e" removal of trace amounts of unreacted N-methylpyrrolidine in the first aqueous solution of MEP causes the pH to reduce to between 6 and 9.

In one embodiment during step "e", N-methylpyrrolidine is removed until its concentration in the first aqueous solution of MEP is less than 2,000 parts per million. In one embodiment during step "e", N-methylpyrrolidine is removed until its concentration in the first aqueous solution of MEP is less than 1,000 parts per million. In one embodiment during step "e", N-methylpyrrolidine is removed until its concentration in the first aqueous solution of MEP is less than 500 parts per million. In one embodiment removal is continued the concentration of N-methylpyrrolidine in the first aqueous solution of MEP is not detectable.

In one embodiment ethyl bromide is removed until its concentration in the first aqueous solution of MEP is not detectable. Removal of the ethyl bromide is preferred to minimize hydrolysis and pH drift of the first aqueous solution of MEP to be less than 6.

The drawings constitute a part of this specification and include exemplary embodiments to the invention, which may be embodied in various forms.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements.

DETAILED DESCRIPTION

Figure 1:
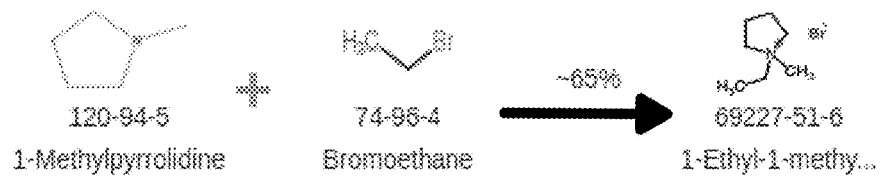
FIG. 1 shows the chemical reaction of N-methylpyrrolidine with ethyl bromide to form MEP.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate system, structure or manner.

Water was used as a solvent in early experiments in making MEP from ethyl bromide and N-methylpyrrolidine. However, hydrolysis occurred between the ethyl bromide and water generating HBr that reacted with the amine forming amine salts and lowering the pH.

Surprisingly, it was discovered that the reaction could be run with an excess of the alkyl halide (e.g., ethyl bromide) to act as both: (i) a solvent and (ii) a reactant. After the reaction is complete and the temperature is lowered to prevent or minimize hydrolysis, deionized water can be added to the reactants causing the formation of two liquid phases. The first aqueous phase has the ionic liquid (e.g., aqueous MEP) and the second organic phase has the remaining excess alkyl halide (e.g., ethyl bromide). The organic phase (e.g., ethyl bromide) can be recycled to the next cycle for forming MEP (e.g., forming an excess of ethyl bromide compared to added N-methylpyrrolidine) and the aqueous phase with ionic liquid can be used as is without requiring removal of a solvent or further purification.

In various embodiments MEP can be made by adding N-methylpyrrolidine to an excess of ethyl bromide as the solvent thereby causing MEP to form as a solid or slurry, and subsequently adding water to dissolve the MEP in the water.

In various embodiments is provided a method of preparing MEP including the steps of: (a) adding N-methylpyrrolidine to an excess amount of ethyl bromide located in a reactor, wherein the N-methylpyrrolidine will react with the ethyl bromide forming MEP, wherein the reaction will have a reaction temperature that can vary over time; (b) stopping addition of N-methylpyrrolidine when the excess of ethyl bromide to the N-methylpyrrolidine falls within a range of 3:1 to 1.5:1; (c) adding water to the reactor creating a two phase system to develop which includes: (i) a top layer containing aqueous MEP and (ii) a bottom layer containing ethyl bromide; (d) separating the top layer from the bottom layer yielding a first aqueous solution of MEP and a layer ethyl bromide; and (e) removing trace amounts of unreacted N-methylpyrrolidine and ethyl bromide from the first aqueous solution of MEP.

In various embodiments, distillation can be used to remove the alkyl halide (e.g., ethyl bromide) from the reaction mass after the water has been added (e.g., removal of ethyl bromide from the two phases of (i) aqueous MEP and (ii) ethyl bromide) but the temperature should remain as low enough to prevent hydrolysis.

The following is an example of a preferred method of making MEP in one embodiment.

1. Obtain the following starting materials:
   (a) ethyl bromide,
   (b) N-methylpyrrolidine, and
   (c) water (preferably distilled, de-ionized, or reverse osmosis)
2. Start with ethyl bromide in a reactor which can be a container, tank, vessel, pressure vessel, pipe, conduit or flask.
3. Add N-methylpyrrolidine to the reactor causing an exothermic reaction with the ethyl bromide tending to increase the temperature. Preferably, the rate of N-methylpyrrolidine added to the reaction is limited to prevent the temperature from exceeding 50° C. Also preferably, during the reaction an excess of ethyl bromide to N-methylpyrrolidine should be maintained in a ratio of least 1.85:1.
4. Discontinue adding N-methylpyrrolidine to the reactor when the excess ratio of ethyl bromide to N-methylpyrrolidine is between 3:1 and 1.5:1. Preferably, addition of N-methylpyrrolidine is stopped when the excess ratio of ethyl bromide to N-methylpyrrolidine is between 2:1 and 1.85:1.
5. Allow the reaction to cool to 25° C. At this point a white slurry of MEP in excess ethyl bromide can be seen in the reactor.

6. Add purified water to the reactor causing the MEP to enter the aqueous phase and creating a 2-phase system:
   (i) a top layer having the MEP dissolved in the added water (with traces of unreacted ethyl bromide and N-methylpyrrolidine), and
   (ii) a bottom layer having ethyl bromide and traces of water.

Purified water can be of several types including without limitation de-ionized water, reverse osmosis water, and distilled water. In one embodiment the water is purified to minimize or eliminate contamination in the two phase system.

7. Separate the upper and bottom layers. Separation can be done by various methods such as using a phase cut of the bottom layer of ethyl bromide (e.g., draw off the bottom layer or draw off the top layer). The recovered bottom layer of ethyl bromide can optionally be reused in the process of forming MEP from adding N-methylpyrrolidine to an excess of ethyl bromide. It is preferred that the recycled ethyl bromide is dried to remove trace water (e.g., drying agent such as magnesium sulfate or distillation).

8. Removal of residual or trace amounts of unreacted ethyl bromide and N-methylpyrrolidine from the aqueous solution of MEP. Removal can be done by various methods such as sparging with a non-reactive gas (such as an inert gas, e.g., $N_2$) and a small amount of heating of the aqueous solution of MEP phase after separation from the ethyl bromide phase. The non-reactive gas is preferably non-reactive relative to MEP, N-methylpyrrolidine, and/or ethyl bromide. For example, the non-reactive gas can be an inert gas such as a noble gas (e.g., $N_2$). Preferably, the sparging is performed at a temperature between 30° C. to 50° C., alternatively between 20° C. to 50° C.; 30° C. to 45° C., or 45° C. to 50° C. The sparging preferably removes trace amounts of unreacted ethyl bromide and N-methylpyrrolidine from the aqueous solution of MEP. The removal of the trace amounts of unreacted N-methylpyrrolidine (which is basic) will reduce the pH of the aqueous solution of MEP. During this removal step, the trace amounts of unreacted N-methylpyrrolidine are removed causing the pH preferably to reduce (e.g., from a starting pH of 11.5 and preferably lowering to a more neutral state such as between 6 and 9). During this removal step, removal of the trace amounts of ethyl bromide will stop hydrolysis of this remaining ethyl bromide which otherwise would cause the pH to drift over time.

EXAMPLES

Example 1 Reaction to Make MEP in Excess Ethyl Bromide as Solvent Then Solvent Swap With Water—Pot Temperature Kept at 40° C. or Less Questions to Answer 1. Can the reaction be run in glassware at atmospheric pressure under reflux solely with an excess ethyl bromide?
2. Can a solvent swap be performed after reaction to replace ethyl bromide with purified (e.g., reverse osmosis) water?
3. Effects of pH on keeping pot temperature <40° C. during solvent swap.
4. What is the yield recovery for ethyl bromide?

FIG. 1 shows the chemical reaction of N-methylpyrrolidine with ethyl bromide to form MEP.

| Experimental Section | | |
|---|---|---|
| Reactants: | | |
| ethyl bromide: | N-methylpyrrolidine | N-methyl-N-ethylpyrrolidinium bromide: CAS #69227-51-6 |
| MW = 108.97 | MW = 85.15 | Pyrrolidinium, 1-ethyl-1-methyl-,bromide |
| Bpt = 38° C. | Bpt = 76-80° C. | 1-methyl-1-ethyl pyrrolidinium-bromide |
| Density = 1.47 | Density = 0.82 | MW 194.11 |

Glass reactor (500 ml 4 neck) setup with overhead stirrer, thermocouple, reflux condenser and pressure equalized dropping funnel.

| Initial Charges | |
|---|---|
| N-methylpyrrolidine: | 85.15 g 1 mole (added via dropping funnel) |
| ethyl bromide: | 218 g (2 moles) |

Solvent Swap
RO Water: 110 g

TABLE 1

Addition of N-methylpyrrolidine Over Time

| Time (am) | Temp (° C.) | N-methyl-pyrrolidine (MP) (mls) | Comments |
|---|---|---|---|
| 7:45 | 18.7 | 0 | start of reaction |
| 7:47 | 20.2 | 20 | |
| 7:56 | 27.4 | 35 | |
| 8:00 | 33.2 | 45 | |
| 8:04 | 43.5 | 70 | ethyl bromide is refluxing |
| 8:08 | 44.2 | 85 | |
| 8:13 | 44.9 | 90 | |
| 8:17 | 45 | 95 | all MP has been added and reaction is starting to cool |
| 8:20 | 45 | | |
| 8:32 | 43.3 | | |
| 9:08 | 38.8 | | |
| 9:30 | 25 | | Added 110 g of RO water and stirred to dissolve all the MEP. MEP is very soluble in water. Phase separated bottom layer to give 106.2 g of ethyl bromide. Top layer set up in distillation mode with an $N_2$ sparge to help remove unreacted trace amounts of ethyl bromide and MP. |
| 10:30 | 36.4 | | |
| 10:34 | 47.7 | | |
| 10:37 | 49.1 | | |
| 10:40 | 49.2 | | |
| 10:52 | 45.3 | | A very small amount of distillate was collected and some hung up in condenser. |

Testing of the MEP provided the following results:

| N-methylpyrrolidine | 240 ppm |
|---|---|
| pH | 9.02 |
| Color APHA | 69 |
| % Water | 48.1% |
| Density: | 1.194 kg/m³ at 22° C. |

TABLE 2

Tested Anions and Cations

| Anion/Cation | Amount Detected (ppm) |
|---|---|
| F | <1 |
| Cl | 9 |
| Br | 264,438 |
| NO$_3$ | <1 |
| PO$_4$ | <1 |
| SO$_4$ | 27 |
| NH$_4$ | N/A |

TABLE 3

AN-3532-HPZB-171
Test Results for Reaction to Make MEP

| Element | Amount Detected Crude (ppm) |
|---|---|
| Ag | <1 |
| Al | <1 |
| As | <1 |
| B | <1 |
| Ba | 7 |
| Be | <1 |
| Ca | <1 |
| Cd | <1 |
| Co | <1 |
| Cr | <1 |
| Cu | <1 |
| Fe | <1 |
| K | <1 |
| Li | <1 |
| Mg | 4 |
| Mn | <1 |
| Mo | <1 |
| Na | 16 |
| Ni | <1 |
| P | <1 |
| Pb | <1 |
| Sb | <1 |
| Se | <1 |
| Si | <1 |
| Sn | <2 |
| Sr | <1 |
| Ti | <1 |
| V | <1 |
| Zn | <3 |

Theoretical composition of Br$^-$ for 65% MEP in water =26.8% (weight percent), and measured was 26.44%

Conclusions

Good quality aqueous solution of MEP product was produced. Literature values for solubility of water in ethyl bromide is listed as 0.896 g/100 mls and solubility of ethyl bromide in water 0.9% at 25° C. Recovered 97% of excess ethyl bromide used, which means only lost 3%. Possible improvement by drying ethyl bromide layer before recycling to next reaction. Can use a nitrogen sparge for removing residual last traces of ethyl bromide from the aqueous phase of MEP.

Example 2: Reaction to Make MEP in 2X Excess Ethyl Bromide Evaluating pH versus Sparge Time Questions to Answer 1. Can the reaction be run in glassware at atmospheric pressure under reflux solely with an excess ethyl bromide?
2. Can a solvent swap be performed after reaction to replace ethyl bromide with purified (e.g., reverse osmosis) water?
3. Effects of pH on keeping pot temperature <40° C. during solvent swap.
4. What is the yield recovery for ethyl bromide?
5. Use of N$_2$ Sparge to remove residual ethyl bromide measure pH versus sparge time at 40° C.

FIG. 1 shows the chemical reaction of N-methylpyrrolidine with ethyl bromide to form MEP.

Experimental Section

Reactants: Same as in Example 1.

Glass reactor (500 ml 4 neck) setup with overhead stirrer, thermocouple, reflux condenser and pressure equalized dropping funnel.

Initial Charges

N-methylpyrrolidine: 85.15 g 1 mole (added via dropping funnel)
ethyl bromide: 218 g (ChemUniverse) 2 moles Solvent Swap RO Water: 110 g

TABLE 4

Reaction HPZB-193: Addition of N-methylpyrrolidine Over Time

| Time (am) | Temp (° C.) | N-methyl-pyrrolidine (MP) (mls) | Comments |
|---|---|---|---|
| 9:00 | 18.3 | 0 | |
| 9:06 | 22.1 | 30 | |
| 9:26 | 41.7 | 50 | |
| 9:31 | 45.2 | 100 | |
| 9:33 | 45.2 | all | |
| 9:40 | 46.0 | | |
| 9:45 | 45.2 | | |
| 10:10 | 41.4 | | |
| 40:48 | 35.6 | | |
| 11.15 | 30 | | Added 110 g of RO water and turned up stirrer speed to dissolve all the MEP. Temp went to 26° C. Performed a phase cut removing the bottom layer. Top layer was 305.76 g and setup for N$_2$ sparge versus time and temperature. |

TABLE 5

N$_2$ Sparging Over Time

| Time (24 hr) | Temp (° C.) | pH | Comments |
|---|---|---|---|
| 11:28 | 23.8 | 11.47 | Turned on heat. |
| 11.33 | 27.8 | 11.27 | |
| 11.36 | 32 | 11.15 | |
| 11.37 | 33.5 | 11.11 | |
| 11.38 | 34.2 | 11.08 | |
| 11.39 | 34.6 | 11.03 | |
| 11.53 | 34.5 | 10.6 | Heat turned up. |
| 12.38 | 49.4 | 9.04 | Heat off. |
| 12.41 | 48.7 | 8.98 | |
| 13.01 | 34.8 | 8.93 | |
| 13:41 | 24.3 | 8.9 | |
| 14:55 | 20.9 | 8.81 | N$_2$ Sparge stopped. 292 g of clear MEP = 96.05% Yield (probably lost some water lost by sparging as well) |

Testing of the MEP provided the following results:

| | |
|---|---|
| N-methylpyrrolidine | 208 ppm |
| pH | 8.65 (day 1) and 8.17 (day 5) |
| Color APHA | 13 |
| % Water | 33.0% |
| Density: | 1.1965 kg/m$^3$ at 21° C. |

TABLE 6

Tested Anions and Cations

| Anion/Cation | Amount Detected (ppm) |
|---|---|
| F | <7 |
| Cl | <13 |
| Br | 272,303 |
| NO$_3$ | <26 |
| PO$_4$ | <39 |
| SO$_4$ | <26 |
| NH$_4$ | <48 |

TABLE 7

AN-3532-HPZB-171
Test Results for Reaction to Make MEP

| Element | Amount Detected Crude (ppm) |
|---|---|
| Ag | <1 |
| Al | <1 |
| As | <1 |
| B | 2 |
| Ba | <1 |
| Be | <1 |
| Ca | <1 |
| Cd | <1 |
| Co | <1 |
| Cr | <1 |
| Cu | <1 |
| Fe | <1 |
| K | 5 |
| Li | <1 |
| Mg | 2 |
| Mn | <1 |
| Mo | <1 |
| Na | <1 |
| Ni | <1 |
| P | <1 |
| Pb | <1 |
| Sb | <1 |
| Se | <1 |
| Si | 5 |
| Sn | <1 |
| Sr | <1 |
| Ti | <1 |
| V | <1 |
| Zn | <1 |

Conclusions

Good quality MEP made with exceptionally low APHA (13) color looking water white. For the comparison of pH versus sparging time it can be seen that the pH is being lowered over time which is believed due to the sparging removal of trace amounts of unreacted N-methylpyrrolidine.

Example 3 To make MEP in excess ethyl bromide as solvent then solvent swap with water Questions to Answer 1. Can the reaction be run in glassware at atmospheric pressure under reflux solely with an excess ethyl bromide?
2. Can a solvent swap be performed after reaction to replace ethyl bromide with purified (e.g., reverse osmosis) water?
3. What is the yield recovery for ethyl bromide?

FIG. 1 shows the chemical reaction of N-methylpyrrolidine with ethyl bromide to form MEP.

Experimental Section

Reactants: Same as in Example 1.

Glass reactor (500 ml 4 neck) setup with overhead stirrer, thermocouple, reflux condenser and pressure equalized dropping funnel.

| Initial Charges | |
|---|---|
| N-methylpyrrolidine: | 85.15 g 1 mole (added via dropping funnel) |
| Ethyl Bromide: | 218 g (VWR) 2 moles |

Solvent Swap
RO Water: 110 g

TABLE 8

Addition of N-methylpyrrolidine Over Time

| Time (am) | Temp (° C.) | N-methyl-pyrrolidine (MP) (mls) | Comments |
|---|---|---|---|
| 8:05 | 19.3 | 0 | 218 g of ethyl bromide placed in the reactor. |
| 8:07 | 20.3 | 10 | Started to add N-methylpyrrolidine dropwise. |
| 8:14 | 23.4 | 15 | |
| 8:22 | 27 | 20 | |
| 8:29 | 33.3 | 30 | |
| 8:31 | 37 | 35 | |
| 8:35 | 40.9 | 35 | Hard reflux of ethyl bromide started so stopped addition of MP to lower reflux. |
| 8:36 | 40.8 | 35 | |
| 8:57 | 38.9 | 35 | Restarted adding MP. |
| 9:04 | 38.9 | 45 | |
| 9:15 | 40.4 | 60 | |
| 9:20 | 42.8 | 80 | |
| 9:31 | 43.7 | all in | |
| 10:20 | 37.7 | | Solid MEP has crashed out of excess ethyl bromide. A white slurry of MEP can be seen. |
| 10:25 | 28.2 | | 110 g of reverse osmosis water was added to dissolve the MEP (perform the solvent swap). In the reactor there is now a top layer of aqueous MEP and a bottom layer of ethyl bromide. |
| | 36.9 | | Setup reactor for distillation and heat applied using an isomantle. Reflux of ethyl bromide started at 36.9° C. |
| | 40.5 | | Hard reflux of ethyl bromide started with lots of distillate being collected by distillation. |
| | 60.1 | | 100 g of ethyl bromide collected (92% recovery based on excess charge) |

Figure 2:
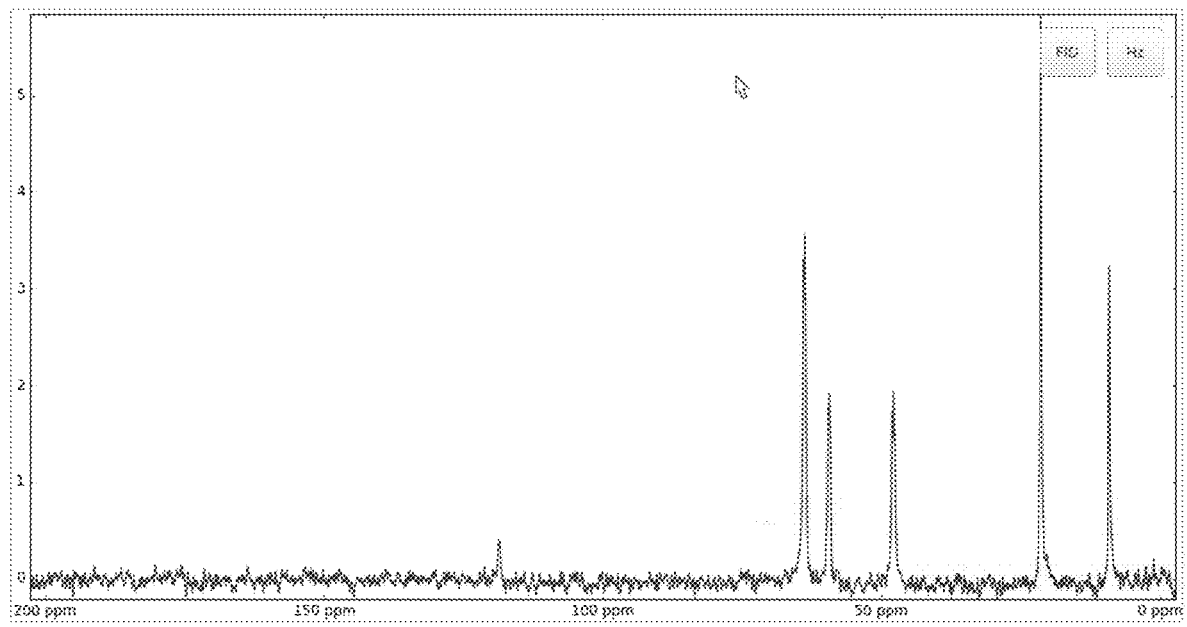
FIG. 2 is a C13 Nuclear magnetic resonance (NMR) spectroscopy of the collected aqueous solution of MEP in CD3CN.

FIG. 2 graphically illustrates various C13 Nuclear magnetic resonance (NMR) spectroscopy testing results on the collected aqueous solution of MEP. The following is a Peak List: 10 peaks:

1: 137 Hz (9.04 ppm)
2: 325 Hz (21.44 ppm)
3: 723 Hz (47.60 ppm)
4: 727 Hz (47.85 ppm)
5: 731 Hz (48.10 ppm)
6: 902 Hz (59.36 ppm)
7: 905 Hz (59.53 ppm)
8: 966 Hz (63.57 ppm)

9: 969 Hz (63.76 ppm)
10: 972 Hz (63.95 ppm)

It is noted that for the collected aqueous solution of MEP there was no sign of N-methylpyrrolidine (it was not detectable in the C13 NMR).

Testing of the MEP provided the following results:

|  | Crude | GAC Treated |
| --- | --- | --- |
| N-methylpyrrolidine | none detected | 76 ppm |
| pH | 6.2 (going to 2.86 on standing) | 5.6 |
| Color APHA | 228 | 117 |
| % Water | N/A | N/A |

Crude is as the MEP came out of the reactor. GAC is after treatment with granulated activated carbon.

TABLE 9

AN-3529-HPZB-167 Test Results for Reaction to Make MEP

| Element | Amount Detected Crude (ppm) | GAC Treated (ppm) |
| --- | --- | --- |
| Ag | <1 | <1 |
| Al | <1 | <1 |
| As | <1 | <1 |
| B | <1 | 3 |
| Ba | <1 | <1 |
| Be | <1 | <1 |
| Ca | <1 | <1 |
| Cd | <1 | <1 |
| Co | <1 | <1 |
| Cr | <1 | <1 |
| Cu | <1 | <1 |
| Fe | <1 | <1 |
| K | <1 | 70 |
| Li | <1 | <1 |
| Mg | <1 | <1 |
| Mn | <1 | <1 |
| Mo | <1 | <1 |
| Na | 45 | 30 |
| Ni | <1 | <1 |
| P | <1 | <1 |
| Pb | <1 | <1 |
| Sb | <1 | <1 |
| Se | <1 | <1 |
| Si | <1 | <1 |
| Sn | <1 | <1 |
| Sr | <1 | <1 |
| Ti | <1 | <1 |
| V | <1 | <1 |
| Zn | <6 | 9 |

Yield: 298 g of pale yellow liquid with pH 6.20
Theory yield =304.11 g (194.11 g MEP plus 110 g water)
Crude Yield =98%
Took 195 g yellow liquid plus 5 g of granulated activated carbon ("GAC") and stirred for 2 hrs then filtered to leave 185 g of a water white liquid. pH 8.34.
~5% loss
Purified yield =93%

Conclusions

During the reaction a non aqueous solvent appears to prevent any hydrolysis products as using water as the solvent to start with causes a small amount of hydrolysis to occur to make HBr and ethanol. The HBr will also make an amine salt which is also undesirable. Completing the reaction in an excess of ethyl bromide and then doing a solvent swap with reverse osmosis water prevents prior hydrolysis.

After distillation about 92% of the excess ethyl bromide was recovered. It is expected that this excess ethyl bromide can be recycled and used in a second process to make MEP.

If released to water, bromoethane will be removed through hydrolysis and volatilization. Aqueous hydrolysis half-lives range from 5 days (at 35° C.) to 21-30 days (at 25° C.). The volatilization half-lives from a model river and pond have been estimated to be 3.2 hours and 38.2 hours, respectively.

If released to soil, bromoethane will be susceptible to hydrolysis under wet soil conditions. Its detection in landfill leachate demonstrates that environmental leaching can occur. Evaporation from moist and dry soils may occur based on its Henry's law constant and a high vapor pressure. Biodegradation of bromoethane is expected to be an important fate process in both water and soil.

It is desired to optimize the purification system for maximizing MEP yield. For example, different amounts of GAC can be used, and washing GAC prior to use plus other absorbents such as alumina can be used. There was an increase in K and a little Zn and Ba increase after GAC treatment.

When compared to experiments using water as solvent-atmospheric pressure to make MEP, the water-solvent prepared aqueous solution of MEP had much lower pH and more color.

Better than doing reaction water as a solvent but still not optimized. Although GAC improves the color of the MEP (from 228 to 117 APHA) the color is still not preferred. Additionally, the pH has improved (2.86 to 5.6), but still not within the preferred range of 6 to 9.

Example 4 Make MEP in Glass Reactor with Water as Solvent Questions to Answer

1. Can the reaction be run in glassware at atmospheric pressure under reflux using water as the solvent?

FIG. 1 shows the chemical reaction of N-methylpyrrolidine with ethyl bromide to form MEP.

Experimental Section

Reactants: Same as in Example 1.

Glass reactor (500 ml 3 neck) setup with magnetic stirrer, thermocouple, and reflux condenser.

| Initial Charges | |
| --- | --- |
| N-methylpyrrolidine: | 85.15 g 1 mole |
| Water | 250 g |
| Ethyl Bromide: | 180 g 1.65 moles (Lot # 1902141030724 from Chem Universe 99.6%) |

TABLE 10

Addition of N-methylpyrrolidine to Water Over Time (slight exotherm from 28 to 31° C.), heat of solution

| Time (am) | Temp (° C.) | N-methyl-pyrrolidine (MP) (mls) | Comments |
| --- | --- | --- | --- |
| 8:40 | 31 | 0 | |
| 8:43 | 31 | 35 | |
| 8:44 | 31 | 75 | |
| 8:45 | 31 | 105 | |
| 9:07 | 49 | 105 | Reflux of ethyl bromide seen so stopped addition of MP to lower reflux. |
| 9:30 | 42 | 135 | |
| 9:40 | 38.8 | 165 | |
| 10:00 | 35 | 180 | Little to no reflux of ethyl bromide. Color is pale yellow. |
| 10:30 | 38 | | Setup reactor for distillation, temperature set at 100° C. |

TABLE 10-continued

Addition of N-methylpyrrolidine to Water Over
Time (slight exotherm from 28 to 31° C.), heat of solution

| Time (am) | Temp (° C.) | N-methyl-pyrrolidine (MP) (mls) | Comments |
|---|---|---|---|
| 10:30 | 102 | | Small amount of distillate came over, mixture now orange 443 g crude MEP in water Theory 444.15 g Crude yield = 99.7% |

Before treatment with of granulated activated carbon ("GAC") the pH is 1.77 and the color is orange. 200 g of the crude MEP was treated with 20 g of GAC for 3 hours and then filtered leaving 179 g of a white liquid with a pH of 5.59.

Testing of the MEP after treatment with GAC provided the following results:

| | |
|---|---|
| N-methylpyrrolidine | 135 ppm |
| pH | 4.48 |
| Color APHA | 126 |

TABLE 11

Tested Anions and Cations

| Anion/Cation | Amount Detected (ppm) |
|---|---|
| F | <1 |
| Cl | 46.3 |
| Br | 168,486 |
| $NO_3$ | <1 |
| $PO_3$ | 103 |
| $SO_4$ | 20.5 |
| $NH_4$ | N/A |

TABLE 12

AN-3520-HPZB-160 Test Results
for Reaction to Make MEP in H2O At Atm

| Element | Amount Detected Crude (ppm) |
|---|---|
| Ag | <1 |
| Al | <1 |
| As | <1 |
| B | <1 |
| Ba | <1 |
| Be | <1 |
| Ca | 13 |
| Cd | <1 |
| Co | <1 |
| Cr | <1 |
| Cu | <1 |
| Cu | <1 |
| Fe | <1 |
| K | 692 |
| Li | <1 |
| Mg | 49 |
| Mn | <1 |
| Mo | <1 |
| Na | 51 |
| Ni | <1 |
| P | <1 |
| Pb | <1 |
| Sb | <1 |
| Se | <1 |

TABLE 12-continued

AN-3520-HPZB-160 Test Results
for Reaction to Make MEP in H2O At Atm

| Element | Amount Detected Crude (ppm) |
|---|---|
| Si | <1 |
| Sn | <1 |
| Sr | <1 |
| Ti | <1 |
| V | <1 |
| Zn | <3 |

This is 194.11 g MEP in total 444.11 g solution giving 43.7% solution in water
Theory wt % $Br^-$=18%.
Found wt % $Br^-$=16.84%

Conclusions

Metals are low due to running reaction in glassware, and preferably would specify a glass lined reactor for making this product. pH is also higher than experiments where the MEP was made with water as the solvent in a 316 SS pressure reactor. APHA color is high and requires GAC treatment. Use of GAC increases amounts of trace metals such as Ca, K, Mg, Na, and Zn which is not preferable. Removal of ethyl bromide by distillation results in an exceptionally low pH aqueous solution of MEP.

Example 5 Make MEP in Glass Reactor With Water as Solvent Questions to Answer

1. Reaction N-methylpyrrolidine with ethyl bromide to make N-methyl-N-ethylpyrrolidinium bromide
2. Use Ethyl bromide in excess (50%)
3. Use water as the solvent
4. Temperature 80° C. for Hours
5. Best isolation procedure (heat solution to flash of excess ethyl bromide)
6. Purity-desire free N-methylpyrrolidine <2000 ppm FIG. 1 shows the chemical reaction of N-methylpyrrolidine with ethyl bromide to form MEP.

Experimental Section

Reactants: Same as in Example 1.

Added ethyl bromide to the reactor, quickly added N-methylpyrrolidine to reactor and buttoned up. Passed $N_2$ subsurface for 5 minutes to flush out all the air then released all pressure and closed all valves. Started stirrer but no heat applied, noted exotherm starting and pressure slowly increasing with temperature.

| Initial Charges | |
|---|---|
| N-methylpyrrolidine: | 85.15 g 1 mole |
| Water | 110 g |
| Ethyl Bromide: | 164 g 1.5 moles |

TABLE 13

Forming MEP

| Time (am) | Reaction Time | Temp (° C.) | psi | Comments |
|---|---|---|---|---|
| 8:00 | | 30 | 4 | Flushed with $N_2$ |
| 8:17 | | 63 | 14 | |
| 8:30 | | 68 | 24 | |
| 9:30 | | 75 | 34 | Max exotherm turned on heat set to 80° C. |
| 9:50 | | 80 | 40 | |
| 12:30 | | 80 | 41 | Heat off and applied cooling |

TABLE 13-continued

Forming MEP

| Time (am) | Reaction Time | Temp (° C.) | psi | Comments |
|---|---|---|---|---|
| 12:36 | about 4 hours at 80° C. | 15 | 10 | Released pressure and emptied liquid from reactor (350 g). |

Results and Discussion 350 g amber liquid (359 g was charged to reactor)

Setup distillation unit, pot temp to 82° C., distilled of 18 g of ethyl bromide 320 g fluid left in pot:

Treated fluid (290 g) with 50 g of GAC for 24 hour then filtered to give a 260 g of a very light colored fluid.

pH 0.14

Testing of the MEP provided the following results:

| pH | 0.14 |
|---|---|
| Color APHA | 149 |

TABLE 14

Tested Anions and Cations

| Anion/Cation | Amount Detected (ppm) |
|---|---|
| F | 4.7 |
| Cl | 53.4 |
| Br | 289,179 |
| $NO_3$ | <1 |
| $PO_3$ | 135 |
| $SO_4$ | 39.2 |
| $NH_4$ | N/A |

TABLE 15

AN-3519-HPZB-156 Test
Results for Reaction to Make MEP in H2O

| Element | Amount Detected Crude (ppm) |
|---|---|
| Ag | 46 |
| Al | <1 |
| As | <1 |
| B | <1 |
| Ba | <1 |
| Be | <1 |
| Ca | 102 |
| Cd | <1 |
| Co | <1 |
| Cr | 104 |
| Cu | <1 |
| Fe | 73 |
| K | 1590 |
| Li | <1 |
| Mg | 172 |
| Mn | 7 |
| Mo | 2 |
| Na | 118 |
| Ni | 52 |
| P | 60 |
| Pb | <1 |
| Sb | <1 |
| Se | <1 |
| Si | 16 |
| Sn | <1 |
| Sr | 2 |
| Ti | <1 |
| V | <1 |
| Zn | <7 |

Conclusions

There was Fe and Cr pickup from 316 SS reactor. Need to do reaction in glass lined steel or other suitable materials to avoid metal pickup. APHA color is high and requires GAC treatment possibly because of the high reaction temperature of 80° C. Use of GAC increases amounts of trace metals. Removal of ethyl bromide by distillation results in an exceptionally low pH aqueous solution of MEP. This is not a preferred method of making MEP.

All measurements disclosed herein are at standard temperature and pressure, at sea level on Earth, unless indicated otherwise.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

I claim:

1. A method of preparing MEP comprising the steps of:
   (a) adding N-methylpyrrolidine to an excess amount of ethyl bromide located in a reactor, wherein the N-methylpyrrolidine will react with the ethyl bromide forming MEP, wherein the reaction will have a reaction temperature that can varies over time;
   (b) stopping addition of N-methylpyrrolidine when the excess of ethyl bromide to the N-methylpyrrolidine falls within a range of 3:1 to 1.5:1;
   (c) adding water to the reactor creating a two phase system to develop which includes: (i) a top layer containing aqueous MEP and (ii) a bottom layer containing ethyl bromide;
   (d) separating the top layer from the bottom layer yielding a first aqueous solution of MEP and a second solution of ethyl bromide; and
   (e) removing N-methylpyrrolidine and ethyl bromide from the first aqueous solution of MEP.

2. The method of preparing MEP of claim 1, wherein during step "a" the reaction temperature is maintained lower than 50° C.

3. The method of preparing MEP of claim 1, wherein step "b" occurs when the excess of ethyl bromide to the N-methylpyrrolidine falls within a range of 3:1 to 1.85:1.

4. The method of preparing MEP of claim 1, wherein step "b" occurs when the excess of ethyl bromide to the N-methylpyrrolidine falls within a range of 2:1 to 1.85:1.

5. The method of preparing MEP of claim 1, wherein during step "b" the excess of ethyl bromide to the N-methylpyrrolidine is of 3:1 to 2:1.

6. The method of preparing MEP of claim 1, wherein and a slurry of MEP is formed in the excess of ethyl bromide in step "b", and the slurry of MEP and excess ethyl bromide is allowed to cool to 25° C. between steps "b" and "c".

7. The method of preparing MEP of claim 1, wherein in step "c" the water is purified water.

8. The method of preparing MEP of claim 7, wherein the purified water is selected from the group consisting of de-ionized water, reverse osmosis water, and distilled water.

9. The method of preparing MEP of claim 1, wherein step "d" is performed using a phase cut.

10. The method of preparing MEP of claim 1, wherein step "e" sparging with a noble gas is used for removal of N-methylpyrrolidine and ethyl bromide.

11. The method of preparing MEP of claim 10, wherein N2 is the noble gas.

12. The method of preparing MEP of claim 1, wherein step "e" sparging with a gas is used for removal of N-methylpyrrolidine and ethyl bromide, wherein said gas is non-reactive relative to MEP, N-methylpyrrolidine, and ethyl bromide.

13. The method of preparing MEP of claim 12, wherein the sparging is performed at a temperature of between 30° C. and 50° C.

14. The method of preparing MEP of claim 12, wherein at the end of step "e" the pH is between 6 and 9.

15. The method of preparing MEP of claim 12, wherein at the end of step "e" the pH is between 6 and 9 due to ethyl bromide.

16. The method of preparing MEP of claim 1, wherein in step "a", the reactor is selected from the group consisting of a container, a tank, a vessel, a pressure vessel, a pipe, a conduit, and a flask.

17. The method of preparing MEP of claim 1, wherein in step "a", the reactor is insulated.

18. The method of preparing MEP of claim 1, wherein in step "a", the reactor is a jacketed vessel.

19. The method of preparing MEP of claim 1, wherein in step "e", N-methylpyrrolidine is removed until its concentration in the first aqueous solution of MEP is less than 2000 parts per million.

20. The method of preparing MEP of claim 19, wherein in step "e", N-methylpyrrolidine is removed until its concentration in the first aqueous solution of MEP is not detectable.

21. The method of preparing MEP of claim 1, wherein in step "e", ethyl bromide is removed until only trace amounts of ethyl bromide remain in the first aqueous solution of MEP.

22. The method of preparing MEP of claim 21, wherein in step "e", ethyl bromide is removed until its concentration in the first aqueous solution of MEP is not detectable.

* * * * *